United States Patent
Chang et al.

(10) Patent No.: US 10,684,226 B2
(45) Date of Patent: Jun. 16, 2020

(54) RAMAN PROBE, RAMAN SPECTRUM OBTAINING APPARATUS, AND METHOD OF OBTAINING RAMAN SPECTRUM AND DETECTING DISTRIBUTION OF TARGET MATERIAL USING RAMAN PROBE

(71) Applicant: SAMSUNG ELECTRONICS CO., LTD., Suwon-si (KR)

(72) Inventors: Ho Jun Chang, Seoul (KR); Woo Chang Lee, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/297,153

(22) Filed: Mar. 8, 2019

(65) Prior Publication Data

US 2019/0277764 A1    Sep. 12, 2019

(30) Foreign Application Priority Data

Mar. 9, 2018 (KR) .......................... 10-2018-0027747
Jan. 8, 2019 (KR) .......................... 10-2019-0002483

(51) Int. Cl.
*G01J 3/44* (2006.01)
*G01N 21/65* (2006.01)

(52) U.S. Cl.
CPC ..... *G01N 21/65* (2013.01); *G01N 2201/0636* (2013.01); *G01N 2201/129* (2013.01)

(58) Field of Classification Search
CPC ........... G01J 3/44; G01N 21/64; G01N 21/65; G01N 2201/129; G01N 2201/0636
See application file for complete search history.

(56) References Cited

U.S. PATENT DOCUMENTS

| | | | |
|---|---|---|---|
| 5,640,957 A | 6/1997 | Kaminski et al. | |
| 6,486,948 B1 | 11/2002 | Zeng | |
| 6,571,117 B1 | 5/2003 | Marbach | |
| 7,328,052 B2 | 2/2008 | Samsoondar et al. | |
| 7,873,397 B2 | 1/2011 | Higgins et al. | |
| 8,355,767 B2 | 1/2013 | Hunter et al. | |
| 2001/0033381 A1* | 10/2001 | Stumbo ............... | B01L 3/50853 356/440 |
| 2003/0191398 A1 | 10/2003 | Motz et al. | |
| 2006/0063991 A1 | 3/2006 | Yu et al. | |
| 2006/0139633 A1 | 6/2006 | Puppets et al. | |
| 2008/0170218 A1 | 7/2008 | Dantus et al. | |
| 2012/0010513 A1 | 1/2012 | Wong et al. | |

(Continued)

FOREIGN PATENT DOCUMENTS

JP    2012-098184 A    5/2012

*Primary Examiner* — Abdullahi Nur
(74) *Attorney, Agent, or Firm* — Sughrue Mion, PLLC

(57) ABSTRACT

A Raman probe provided includes a light source part configured to emit light on a sample, and further configured to adjust at least one of an incident angle of the light, a position of an emission point of the light, and a focal point of the light source part, a light collector configured to collect Raman scattered light from the sample, and further configured to adjust a field of view of Raman measurement and a focal point of the light collector, and a photodetector configured to receive the collected Raman scattered light, wherein the light source part comprises a reflection mirror configured to rotate to adjust the position of the emission point of the light.

16 Claims, 8 Drawing Sheets

(56) References Cited

U.S. PATENT DOCUMENTS

| | | | |
|---|---|---|---|
| 2014/0132950 A1* | 5/2014 | Nakata | G01N 21/65 |
| | | | 356/72 |
| 2014/0200434 A1 | 7/2014 | Cheng | |
| 2014/0204378 A1* | 7/2014 | Day | G01J 3/2823 |
| | | | 356/326 |
| 2015/0060673 A1 | 3/2015 | Zimdars | |
| 2016/0235345 A1 | 8/2016 | Perez Calero et al. | |
| 2017/0122948 A1* | 5/2017 | Schuetze | G01N 21/65 |
| 2017/0127983 A1 | 5/2017 | Spegazzini et al. | |

* cited by examiner

RAMAN PROBE, RAMAN SPECTRUM OBTAINING APPARATUS, AND METHOD OF OBTAINING RAMAN SPECTRUM AND DETECTING DISTRIBUTION OF TARGET MATERIAL USING RAMAN PROBE

CROSS-REFERENCE TO RELATED APPLICATION(S)

This application claims priority from Korean Patent Application No. 10-2018-0027747, filed on Mar. 9, 2018, in the Korean Intellectual Property Office, and Korean Patent Application No. 10-2019-0002483, filed on Jan. 8, 2019, in the Korean Intellectual Property Office, the entire disclosures of which are incorporated herein by reference.

BACKGROUND

1. Field

Example embodiments of the present disclosure relate to a Raman probe, a Raman spectrum obtaining apparatus, and a method of obtaining a Raman spectrum and detecting distribution of a target material using the Raman probe.

2. Description of the Related Art

Non-invasive glucose sensors, using spectroscopic techniques such as Raman spectroscopy, may improve convenience of patients with diabetes or people at risk for metabolic diseases who are required to perform frequent finger prick tests. Particularly, such non-invasive analysis techniques may be used to predict a signal of a blood component by analyzing interstitial fluid present in a dermal layer based on each individual skin spectrum. However, the obtained skin spectrum is mixed with a signal derived from biomolecules, e.g., lipid, protein, etc., which pass through an incident light path, e.g., dead skin cells, epidermis layer, dermis layer, etc., such that the obtained skin spectrum may have greater background noise than a signal of a target material (e.g., glucose).

SUMMARY

One or more example embodiments provide a Raman probe, a Raman spectrum obtaining apparatus, and a method of obtaining a Raman spectrum and detecting distribution of a target material using the Raman probe.

According to an aspect of an example embodiment, there is provided a Raman probe including a light source part configured to emit light on a sample, and further configured to adjust at least one of an incident angle of the light, a position of an emission point of the light, and a focal point of the light source part, a light collector configured to collect Raman scattered light from the sample, and further configured to adjust a field of view of Raman measurement and a focal point of the light collector, and a photodetector configured to receive the collected Raman scattered light, wherein the light source part comprises a reflection mirror configured to rotate to adjust the position of the emission point of the light.

The light source part may be configured to move back and forth, from side to side, and up and down, or rotate.

The light source part may further include at least one light source configured to emit light of predetermined wavelengths, and a filter configured to select light of a specific wavelength from among light beams emitted by the light source.

The light source part may be provided at a side surface of the light collector.

The light collector may be configured to move up and down.

The Raman probe may further include an actuator configured to move or rotate the light source part, or to move the light collector.

According to an aspect of an example embodiment, there is provided a method of obtaining a Raman spectrum using a Raman probe configured to adjust an incident angle of light emitted on a sample and a position of an emission point of the light, the method including adjusting at least one of an incident angle of the light emitted on the sample and the position of the emission point of the light, obtaining a Raman spectrum of the sample, determining a similarity between the Raman spectrum and a stored Raman spectrum of a target material, and storing the incident angle of the light emitted on the sample, the position of the emission point of the light, and the Raman spectrum based on the determination of similarity.

The adjusting may include adjusting at least one from among the incident angle of the light and the position of the emission point of the light by moving a light source part of the Raman probe back and forth, from side to side, and up and down, or by rotating the light source part.

The determining may include determining the similarity using one from among Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

The storing may include, based on the similarity being greater than a predetermined threshold value, storing the incident angle of the light emitted onto the sample, the position of the emission point of the light, and the Raman spectrum based on the similarity being greater than a predetermined threshold value.

The method may further include, based on the similarity being less than or equal to a predetermined threshold value, repeating the adjusting, the obtaining, and the determining.

According to an aspect of an example embodiment, there is provided a method of detecting distribution of a target material using a Raman probe configured to adjust an incident angle of light emitted by a light source part on a sample, a focal point of the light source part, a field of view of a light collector, and a focal point of the light collector, the method including obtaining a first Raman spectrum of the sample by setting the focal point of the light collector on a surface of the sample, obtaining a second Raman spectrum of the sample by adjusting the field of view of the light collector, determining a similarity between the first Raman spectrum and the second Raman spectrum, and storing position information of the light source part and the light collector, and the second Raman spectrum based on the determination of similarity.

The obtaining of the first Raman spectrum of the sample may include setting the focal point of the light collector on the surface of the sample by moving the light collector up and down.

The obtaining of the second Raman spectrum of the sample may include adjusting the field of view of the light collector by moving the light collector up and down.

The determining of the similarity may include determining the similarity using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

The storing of the position information of the light source part and the light collector, and the second Raman spectrum may include, based on the similarity being less than or equal to a predetermined threshold value, storing the position information of the light source part and the light collector, and the second Raman spectrum.

The method may further include, based on the similarity being greater than a predetermined threshold value, determining whether the focal point of the light source part is the same as the focal point of the light collector, and based on the focal point of the light source part being the same as the focal point of the light collector, repeating the obtaining of the first Raman spectrum of the sample by adjusting the focal point of the light source part, the obtaining of the second Raman spectrum of the sample, the determining of the similarity between the first Raman spectrum and the second Raman spectrum, and the determining whether the focal point of the light source part is the same as the focal point of the light collector.

The method may further include, based on the focal point of the light source part not being equal to the focal point of the light collector, obtaining a third Raman spectrum of the sample by adjusting the field of view of the light collector, determining a similarity between the second Raman spectrum and the third Raman spectrum, and storing position information of the light source part and the light collector, and the third Raman spectrum based on the determination of similarity.

The light source part may be configured to adjust the incident angle of the light based on an interference occurring between the light emitted by the light source part and the light collected by the light collector.

The method may further include determining whether interference occurs between light emitted by the light source part and the light collected by the light collector, and adjusting the incident angle of light based on determining that the interference occurs.

Figure 1:
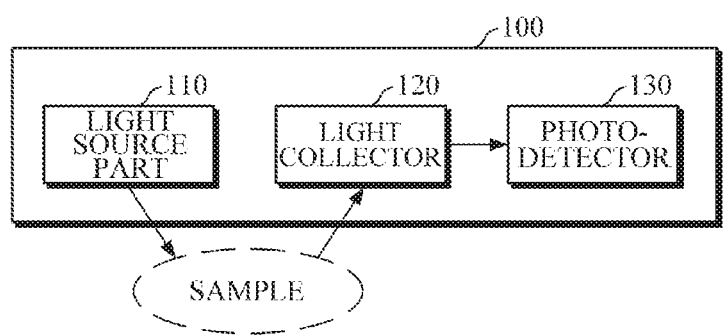
FIG. 1 is a block diagram illustrating a Raman probe according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, example embodiments of the present disclosure will be described in detail with reference to the accompanying drawings. It should be noted that wherever possible, the same reference symbols refer to same parts, even in different drawings.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the operations according to exemplary embodiments, and can be varied according to a purpose of a user or manager, or precedent and so on.

It will be understood that, although the terms first, second, etc. may be used herein to describe various elements, these elements should not be limited by these terms. These terms are only used to distinguish one element from another. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to operations mainly performed by the components. That is, two or more components can be integrated into a single component. Furthermore, a single component can be separated into two or more components. Moreover, each component which will be described can additionally perform some or all of an operation executed by another component in addition to the main operation thereof. Some or all of the main operation of each component which will be explained can be carried out by another component.

Expressions such as "at least one of", when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating a Raman probe according to an example embodiment.

Referring to FIG. 1, the Raman probe 100 includes a light source part 110, a light collector 120, and a photodetector 130.

The light source part 110 may emit light onto a sample. The light source part 110 may include at least one or more light sources. For example, the light source may emit light of a predetermined wavelength, e.g., visible light or infrared light, onto a sample. However, the light emitted is not limited thereto, and various wavelengths of light to be emitted by the light source may vary depending on the purpose of measurement, types of an analyte, and the like. Further, each light source is not necessarily a single light emitting body, and may be formed as an array of a plurality of light emitting bodies. In the case where each light source is formed as an array of a plurality of light emitting bodies, the plurality of light emitting bodies may emit light of different wavelengths or may emit light of the same wavelength to be suitable for the purpose of measurement. According to an example embodiment, the light source may include a light-emitting diode (LED), a laser diode, and the like. However, this is merely exemplary, and the light source is not limited thereto.

According to an example embodiment, the light source part 110 may further include a filter, e.g., a long pass filter, a clean-up filter, a bandpass filter, etc., for selecting light of a specific wavelength, or an optical element, e.g., a reflection mirror, etc., for directing the emitted light toward a desired position of a sample.

The light source part 110 may be configured to adjust at least one of an incident angle of light emitted onto a sample, a position of an emission point of the light, and a focal point of the light source part 110. For example, the light source part 110 or components of the light source part 110, e.g., a light source, a reflection mirror, etc., may be configured to move up and down, from side to side, and back and forth, or to rotate.

The light collector 120 may collect Raman scattered light from the sample. The light collector 120 may include a filter, e.g., a long pass filter, a clean-up filter, etc., a lens, e.g., a collimating lens, a focusing lens, etc., a fiber, a waveguide, a grating, and the like.

The light collector 120 may be configured to adjust a field of view of the Raman measurements, and a focal point of the light collector 120. For example, the light collector 120 or components of the light collector 120, e.g., a filter, a lens, etc., may be configured to move up and down.

The photodetector 120 may receive the Raman scattered light collected by the light collector 120. According to an example embodiment, the photodetector 120 may include a photo diode, a photo transistor (PTr), a charge-coupled device (CCD), or the like. The photodetector 130 is not necessarily a single device, and may be formed as an array of a plurality of devices.

Figure 2:
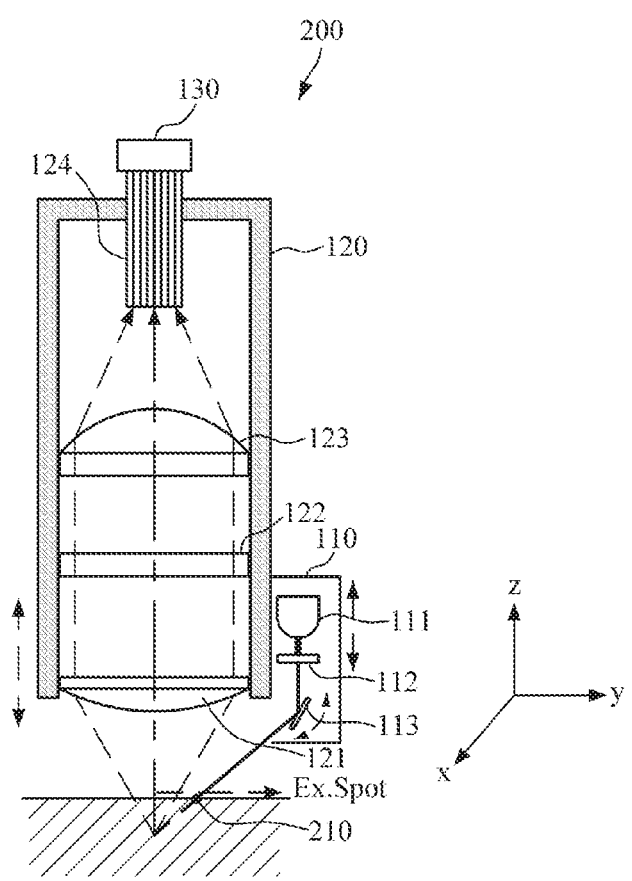
FIG. 2 is a diagram illustrating a structure of a Raman probe according to an example embodiment.

FIG. 2 is a diagram illustrating an example of a structure of a Raman probe. The Raman probe 200 of FIG. 2 may be an example of the Raman probe 100 of FIG. 1.

Referring to FIG. 2, the Raman probe 200 includes a single light source part 110, a light collector 120, and a photodetector 130.

The single light source part 110 may emit light onto a sample obliquely from the side of the light collector 120.

The light source part 110 may include a light source 111, a clean-up filter 112, and a reflection mirror 113. According to an example embodiment, the light source 111, the clean-up filter 112, and the reflection mirror 113 may individually move up and down, from side to side, and back and forth, or rotate. However, the movement is not limited thereto, and the entire light source part 110 may move up and down in a z-axis direction, from side to side in an y-axis direction, and back and forth in an x-axis direction, or rotate The light collector 120 may include a collimating lens 121, a long pass filter 122, a focusing lens 123, and a fiber 124. According to an example embodiment, the collimating lens 121, the long pass filter 122, the focusing lens 123, and the fiber 124 may individually move up and down. However, the movement is not limited thereto, and the entire light collector 120 may move up and down.

Figure 3:
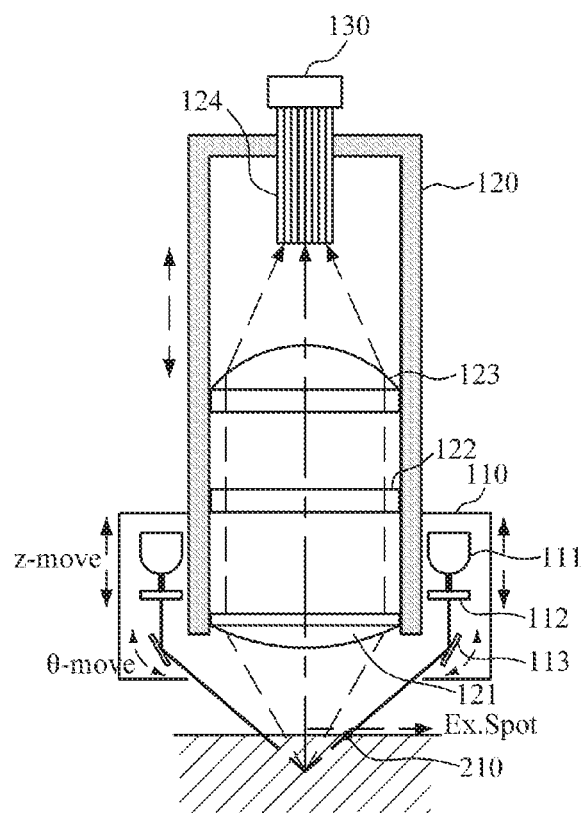
FIG. 3 is a diagram illustrating a structure of a Raman probe according to an example embodiment.

FIG. 3 is a diagram illustrating a structure of a Raman probe according to an example embodiment. The Raman probe 300 of FIG. 3 may be an example of the Raman probe 100 of FIG. 1.

Referring to FIG. 3, the Raman probe 200 includes a plurality of light source parts 110, a light collector 120, and a photodetector 130. Here, the light source parts 110, the light collector 120, and the photodetector 130 are described above with reference to FIGS. 1 and 2, such that detailed description thereof will be omitted.

In the example of FIG. 3, the plurality of light source parts 110 are disposed to surround the light collector 120, to emit light onto the sample obliquely from the side of the light collector 120.

In addition, the Raman probes of FIGS. 2 and 3 are merely examples of the Raman probe 100 of FIG. 1. That is, the configuration of the light source parts 110 and the light collector 120 is not limited to the examples illustrated in FIGS. 2 and 3.

Figure 4:
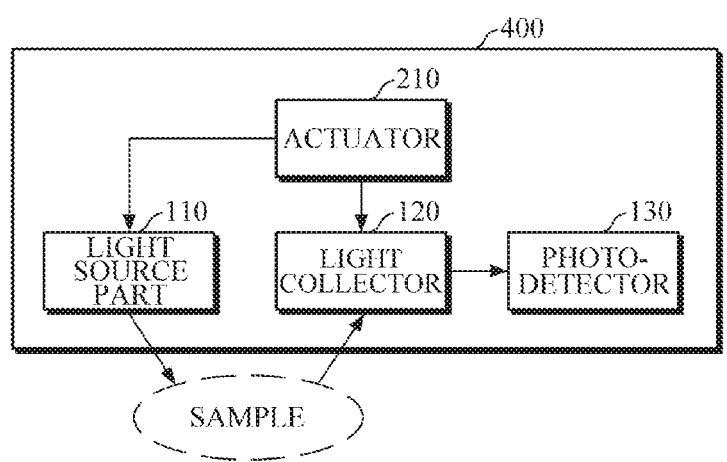
FIG. 4 is a block diagram illustrating a Raman probe according to an example embodiment.

FIG. 4 is a block diagram illustrating a Raman probe according to an example embodiment.

Referring to FIG. 4, the Raman probe 400 includes a light source part 110, a light collector 120, a photodetector 130, and an actuator 210. Here, the light source part 110, the light collector 120, and the photodetector 130 are described above with reference to FIGS. 1 to 3, such that detailed description thereof will be omitted.

The actuator 210 may move or rotate the light source part 110 and the light collector 120 according to a predetermined control signal. For example, the actuator 210 may move the light source part 110 up and down, from side to side, or back and forth, or may rotate the light source part 110 according to a predetermined control signal. Further, the actuator 210 may move the light collector 120 up and down according to a predetermined control signal.

Figure 5:
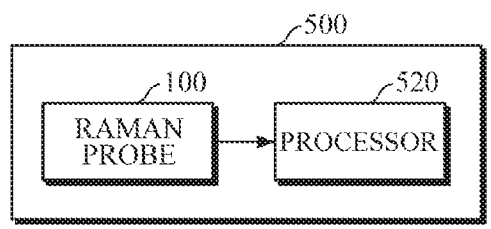
FIG. 5 is a block diagram illustrating a Raman spectrum obtaining apparatus according to an example embodiment.

FIG. 5 is a block diagram illustrating a Raman spectrum obtaining apparatus according to an example embodiment. Referring to FIG. 5, the Raman spectrum obtaining apparatus 500 includes a Raman probe 100 and a processor 520. Here, the Raman probe 100 is described above with reference to FIGS. 1 to 4, such that detailed description thereof will be omitted.

The processor 520 may control the overall operation of the Raman spectrum obtaining apparatus 500, and may process various signals associated with the operation of the Raman spectrum obtaining apparatus 500.

The processor 520 may obtain a Raman spectrum of a sample based on Raman scattered light received from the Raman probe 100.

The processor 520 may control the Raman probe 100 to determine an optical Raman probe parameter for measuring a target material, and may obtain an optimal Raman spectrum using the determined Raman probe parameter. In this case, the Raman probe parameter may include a light source part parameter and a light collector parameter, in which the light source part parameter may include a position and an angle of the light source part or components of the light source part, an incident angle of light emitted by the light source part and a position of an emission point of the light, a focal point of the light source part, and the like, and the light collector parameter may include a position of the light collector or components of the light collector, a field of view of the light collector, a focal point of the light collector, and the like.

According to an example embodiment, the processor 520 may obtain a Raman spectrum by adjusting a Raman probe parameter, and may determine an optical Raman probe parameter for measuring a target material based on a similarity between the obtained Raman spectrum and a pre-stored Raman spectrum of a target material. For example, the processor 520 may control the Raman probe 100 to obtain a Raman spectrum of a sample by adjusting a light source part parameter, e.g., an incident angle of light emitted onto the sample and/or a position of an emission point of the light, etc., and may compare the obtained Raman spectrum with the pre-stored Raman spectrum of the target material determine a similarity therebetween. In this case, the processor 520 may use various similarity calculation algorithms including Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and the like. Further, in response to a similarity between the obtained Raman spectrum and the pre-stored Raman spectrum of the target material exceeding a predetermined threshold value, the processor 520 may determine a parameter at that time, e.g., an incident angle of light and a position of an emission point of the light, to be an optimal Raman probe parameter. Further, in response to a similarity between the obtained Raman spectrum and the pre-stored Raman spectrum of the target material being less than or equal to a predetermined threshold value, the processor 520 may repeat the processes of adjusting the light source part parameter and obtaining the Raman spectrum until the similarity between the obtained Raman spectrum and the pre-stored Raman spectrum of the target material exceeds a predetermined threshold value.

The processor 520 may adjust a focusing depth of light emitted by the light source by adjusting the light source part parameter, e.g., a position and an angle of the light source part or components of the light source part, a focal point of the light source part, etc., and may measure a Raman spectrum at various focusing depths. For example, the processor 520 may measure the Raman spectrum at various focusing depths by measuring the Raman spectrum while moving the light source part or components of the light source part in a direction perpendicular to a sample (z-axis direction). Further, the processor 520 may estimate the concentration of an in vivo component by analyzing the Raman spectrum measured at various depths. In this case, the in vivo component may include at least one of glucose, triglycerides, urea, uric acid, lactate, protein, cholesterol, and ethanol. That is, the Raman spectrum obtaining apparatus 500 according to an example embodiment of the present disclosure may estimate the concentration of an in vivo component of a sample more precisely by measuring and analyzing the Raman spectrum at various depths.

The processor 520 may control the Raman probe 100 to detect the distribution of a target material. According to an example embodiment, the processor 520 may detect the distribution of the target material by obtaining the Raman spectrum of the sample while adjusting a position and a focal point of the light source part, and a position, a focal point, and a field of view of the light collector. For example, the processor 520 may control the Raman probe 100 to primarily obtain a Raman spectrum by positioning a focal point of the light source part in a predetermined region below the surface of a sample, and positioning a focal point of the light collector on the surface of the sample; and may secondarily obtain a Raman spectrum by adjusting the field of view of the light collector. In addition, the processor 520 may compare the primarily obtained Raman spectrum with the secondarily obtained Raman spectrum to determine a similarity therebetween. In this case, the processor 520 may use various similarity calculation algorithms including Euclidean distance, Manhattan Distance, Cosine Distance, Mahalanobis Distance, Jaccard Coefficient. Extended Jaccard Coefficient, Pearson's Correlation Coefficient, and Spearman's Correlation Coefficient, and the like. In response to a similarity between the primarily obtained Raman spectrum and the secondarily obtained Raman spectrum being less than or equal to a predetermined threshold value, the processor 520 may terminate detection of the distribution of the target material, and may store the Raman probe parameter, positions of the light source part and the light collector, at that time, and the secondarily obtained Raman spectrum. Further, in response to a similarity between the primarily obtained Raman spectrum and the secondarily obtained Raman spectrum exceeding a predetermined threshold value, the processor 520 determines whether a focal point of the light source part is the same as a focal point of the light collector, and upon determining that the focal points are the same, the processor 520 may repeat the processes of primarily obtaining the Raman spectrum of the aforementioned sample by adjusting the focal point of the light source part, secondarily obtaining the Raman spectrum of the sample, determining a similarity between the primarily obtained Raman spectrum and the secondarily obtained Raman spectrum, and determining whether the focal point of the light source part is the same as the focal point of the light collector. Further, upon determining that the focal points are not the same, the processor 520 may obtain the Raman spectrum of the sample by adjusting the field of view of the light collector, may determine a similarity between the secondarily obtained Raman spectrum and the tertiarily obtained Raman spectrum, and may repeat the above processes based on the determination of similarity.

In addition, the Raman spectrum obtaining apparatus 500 may determine whether interference occurs between light emitted by the light source part and Raman scattered light collected by the light collector in the process of obtaining the Raman spectrum, and upon determining that interference occurs therebetween, the Raman spectrum obtaining apparatus 500 may adjust the light source part parameter, e.g., an incident angle of light, to prevent or reduce the occurrence of interference.

Figure 6:
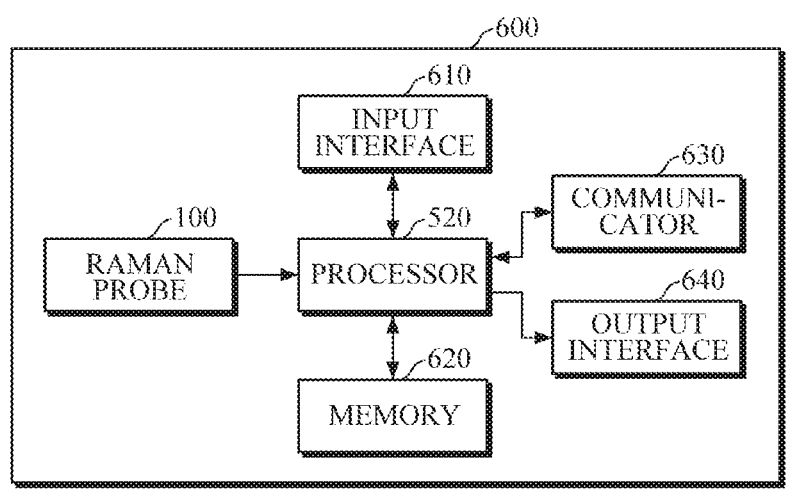
FIG. 6 is a block diagram illustrating a Raman spectrum obtaining apparatus according to an example embodiment.

FIG. 6 is a block diagram illustrating a Raman spectrum obtaining apparatus according to an example embodiment. Referring to FIG. 6, the Raman spectrum obtaining apparatus 600 includes a Raman probe 100, a processor 520, an input interface 610, a memory 620, a communicator 630, and an output interface 640. Here, the Raman probe 100 and the processor 520 are described above with reference to FIGS. 1 to 5, such that detailed description thereof will be omitted.

The input interface 610 may receive input of various operation signals from a user. According to an example embodiment, the input interface 610 may include a keypad, a dome switch, a touch pad or a touch screen w (a static pressure type/a capacitance type), a jog wheel, a jog switch, a hardware (H/W) button, and the like.

The memory 620 may store programs or commands for operation of the Raman spectrum obtaining apparatus 600, and may store data input to and output from the Raman spectrum obtaining apparatus 600. Further, the memory 620 may store the Raman probe parameter determined by the processor 520, the obtained Raman spectrum, and the like.

The memory 620 may include at least one storage medium of a flash memory type memory, a hard disk type memory, a multimedia card micro type memory, a card type memory (e.g., an SD memory, an XD memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like. Further, the Raman spectrum obtaining apparatus 600 may operate an external storage medium, such as web storage and the like, which performs a storage function of the memory 620 on the Internet.

The communicator 630 may perform communication with an external device. For example, the communicator 630 may transmit, to the external device, data input by a user through the input interface 610, the Raman probe parameter determined by the processor 520, the obtained Raman spectrum, and the like, or may receive, from the external device, various data useful for determining the Raman probe parameter, and obtaining the Raman spectrum.

In this case, the external device may be, for example, a medical equipment using the data input by a user through the input interface 610, the Raman probe parameter determined by the processor 520, the obtained Raman spectrum, and the like, a printer to print out results, or a display to display the results. In addition, the external device may be a digital television (TV), a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 630 may communicate with an external device by using Bluetooth communication, Bluetooth low energy (BLE) communication, near field communication (NFC), WLAN communication, Zigbee communication, infrared data association (IrDA) communication, Wi-Fi Direct (WFD) communication, ultra-wideband (UWB) communication, Ant+ communication, WIFI communication, radio frequency identification (RFID) communication, 3G communication, 4G communication, 5G communication, and the like. However, example embodiments are not limited thereto.

The output interface 640 may output the data input by a user through the input interface 610, the Raman probe parameter determined by the processor 520, the obtained Raman spectrum, and the like. According to an example embodiment, the output interface 640 may output the data input by a user through the input interface 610, the Raman probe parameter determined by the processor 520, the obtained Raman spectrum, and the like by using at least one of an acoustic method, a visual method, and a tactile method. For example, the output interface 640 may include a display, a speaker, a vibrator, and the like.

Figure 7:
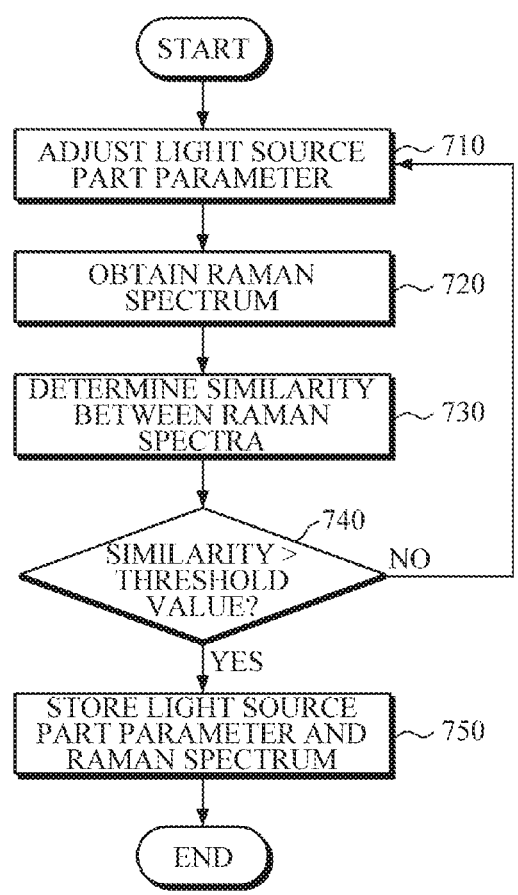
FIG. 7 is a flowchart illustrating a method of obtaining a Raman spectrum using a Raman probe according to an example embodiment.

FIG. 7 is a flowchart illustrating a method of obtaining a Raman spectrum using a Raman probe according to an example embodiment. The Raman spectrum obtaining method of FIG. 7 may be performed by the Raman spectrum obtaining apparatus 500 of FIG. 5.

Referring to FIGS. 5 and 7, the Raman spectrum obtaining apparatus 500 may adjust a light source part parameter, e.g., an incident angle of light emitted onto a sample and/or a position of an emission point of the light, etc. in 710, and may obtain a Raman spectrum of a sample in 720. For example, the Raman spectrum obtaining apparatus 500 may adjust the light source part parameter by moving the light source part of the Raman probe up and down, from side to side, and back and forth, or by rotating the light source part.

The Raman spectrum obtaining apparatus 500 may compare the obtained Raman spectrum with a pre-stored Raman spectrum of a target material, and may determine a similarity therebetween in 730. In this case, the Raman spectrum obtaining apparatus 500 may use various similarity calculation algorithms including Euclidean distance, Manhattan Distance. Cosine Distance, Mahalanobis Distance. Jaccard Coefficient, Extended Jaccard Coefficient, Pearson's Correlation Coefficient, and Spearman's Correlation Coefficient, and the like.

In response to a similarity between the obtained Raman spectrum and the pre-stored Raman spectrum of the target material exceeding a predetermined threshold value in 740, the Raman spectrum obtaining apparatus 500 may determine a light source part parameter at that time, e.g., an incident angle of light and a position of an emission point of the light, to be an optimal Raman probe parameter, and may store the light source part parameter and the Raman spectrum in 750.

By contrast, in response to a similarity between the obtained Raman spectrum and the pre-stored Raman spectrum of the target material being less than a predetermined threshold value in 740, the Raman spectrum obtaining apparatus 500 may return to the operation 710, and may adjust the light source part parameter.

Figure 8:
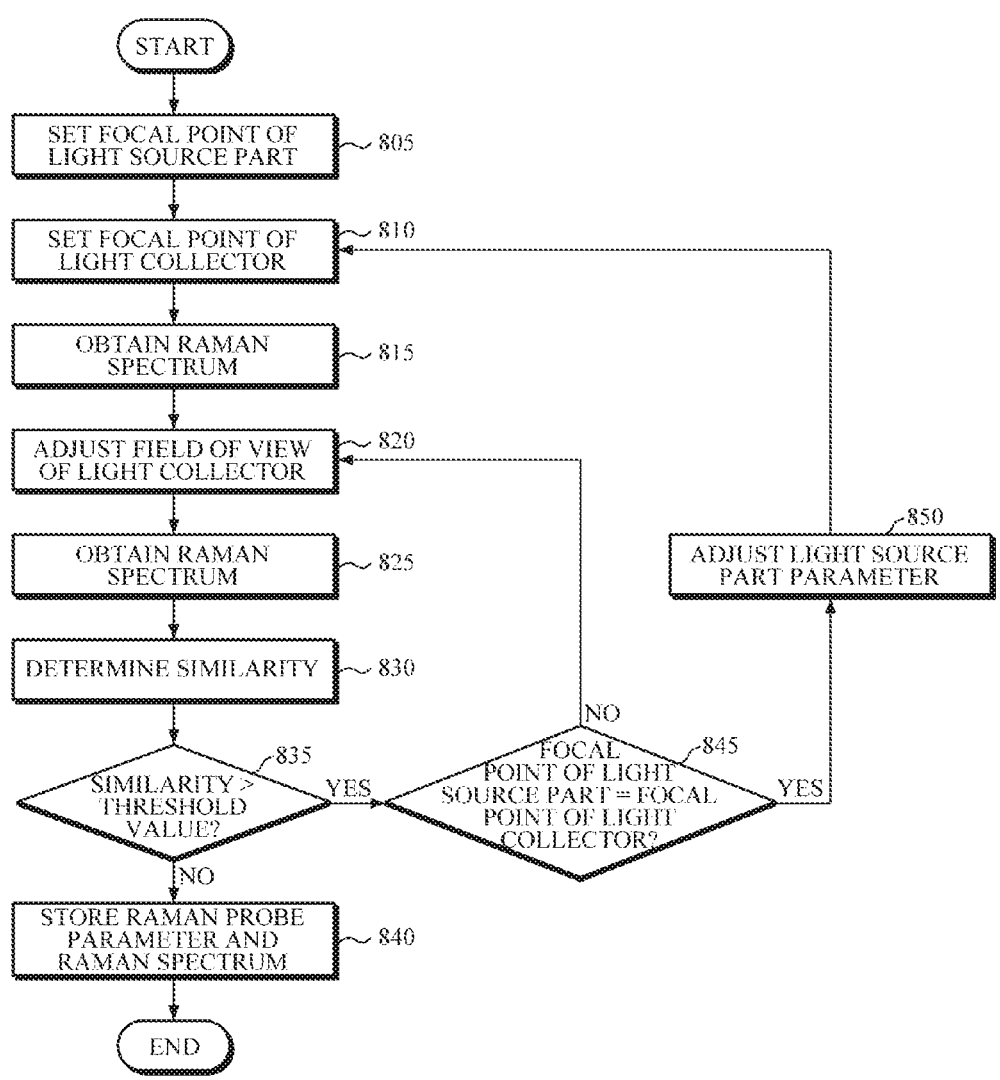
FIG. 8 is a flowchart illustrating a method of detecting distribution of a target material using a Raman probe according to an example embodiment.

FIG. 8 is a flowchart illustrating a method of detecting distribution of a target material using a Raman probe according to an example embodiment. The method of detecting distribution of a target material of FIG. 8 may be performed by the Raman spectrum obtaining apparatus 500 of FIG. 5.

Referring to FIGS. 5 and 8, the Raman spectrum obtaining apparatus 500 may set a focal point of the light source part in a predetermined region below the surface of a sample in 805, and may set a focal point of the light collector on the surface of a sample in 810, to primarily obtain a Raman spectrum in 815. For example, the Raman spectrum obtaining apparatus 500 may set a focal point of the light source part in a predetermined region below the surface of a sample by moving the light source part up and down, and may set a focal point of the light collector on the surface of a sample by moving the light collector up and down.

The Raman spectrum obtaining apparatus 500 may adjust a field of view of the light collector in 820 to secondarily obtain a Raman spectrum in 825. For example, the Raman spectrum obtaining apparatus 500 may adjust the field of view of the light collector by moving the light collector up and down.

The Raman spectrum obtaining apparatus 500 may compare the primarily obtained Raman spectrum with the secondarily obtained Raman spectrum to determine a similarity therebetween in 830. In this case, the Raman spectrum obtaining apparatus 500 may use various similarity calculation algorithms including Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient, and the like.

In response to a similarity between the primarily obtained Raman spectrum and the secondarily obtained Raman spectrum being less than a predetermined threshold value in 835, the Raman spectrum obtaining apparatus 500 may terminate detection of the distribution of the target material, and may store the Raman probe parameter, e.g., positions of the light source part and the light collector, at that time, and the secondarily obtained Raman spectrum in 840.

By contrast, in response to a similarity between the primarily obtained Raman spectrum and the secondarily obtained Raman spectrum exceeding a predetermined threshold value in 835, the Raman spectrum obtaining apparatus 500 may determine whether a focal point of the light source part is the same as a focal point of the light collector in 845, and upon determining that the focal points are the same, the Raman spectrum obtaining apparatus 500 may adjust a light source part parameter, e.g., a focal point of the light source part, in 850, and may return to the operation 810 to set a focal point of the light collector on the surface of a sample.

Upon determining in 845 that the focal point of the light source part is not the same as the focal point of the light collector, the Raman spectrum obtaining apparatus 500 may return to the operation 820, and may adjust a field of view of the light collector to tertiarily obtain a Raman spectrum of a sample in 825, and may determine a similarity between the secondarily obtained Raman spectrum and the tertiarily obtained Raman spectrum in 830.

In addition, the Raman spectrum obtaining apparatus 500 may determine whether interference occurs between light emitted by the light source part and light collected by the light collector in the process of obtaining the Raman spectra in 815 and 825; and upon determining that interference occurs therebetween, the Raman spectrum obtaining apparatus 500 may adjust the light source part parameter, e.g., an incident angle of light, to prevent or reduce the occurrence of interference.

The present disclosure can be realized as a computer-readable code written on a computer-readable recording medium. Codes and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

While example embodiments have been described with reference to the figures, it will be understood by one of ordinary skill in the art that various changes in form and details may be made therein without departing from the spirit and scope of the present disclosure as defined by the following claims.

What is claimed is:

1. A Raman probe comprising:
    a light source part configured to emit light on a sample, and further configured to adjust at least one of an incident angle of the light, a position of an emission point of the light, and a focal point of the light source part;
    a light collector configured to collect Raman scattered light from the sample, and further configured to adjust a field of view of Raman measurement and a focal point of the light collector; and
    a photodetector configured to receive the collected Raman scattered light,
    wherein the light source part comprises a reflection mirror configured to rotate to adjust the position of the emission point of the light,
    wherein the light source part is provided at a side surface of the light collector, and
    wherein the light collector is configured to move up and down.

2. The Raman probe of claim 1, wherein the light source part is configured to move back and forth, from side to side, and up and down, or rotate.

3. The Raman probe of claim 1, wherein the light source part further comprises:
    at least one light source configured to emit light of predetermined wavelengths; and
    a filter configured to select light of a specific wavelength from among light beams emitted by the light source part.

4. The Raman probe of claim 1, further comprising an actuator configured to move or rotate the light source part, or to move the light collector.

5. The Raman probe of claim 1, wherein the light source part is configured to adjust the incident angle of the light based on an interference occurring between the light emitted by the light source part and the light collected by the light collector.

6. A method of obtaining a Raman spectrum using a Raman probe configured to adjust an incident angle of light emitted on a sample and a position of an emission point of the light, the method comprising:
    adjusting at least one of an incident angle of the light emitted on the sample and the position of the emission point of the light;
    obtaining a Raman spectrum of the sample;
    determining a similarity between the Raman spectrum and a stored Raman spectrum of a target material; and
    storing the incident angle of the light emitted on the sample, the position of the emission point of the light, and the Raman spectrum based on the similarity being greater than a predetermined threshold value.

7. The method of claim 6, wherein the adjusting comprises adjusting at least one from among the incident angle of the light and the position of the emission point of the light by moving a light source part of the Raman probe back and forth, from side to side, and up and down, or by rotating the light source part.

8. The method of claim 6, wherein the determining comprises determining the similarity using one from among Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

9. The method of claim 6, further comprising, based on the similarity being less than or equal to the predetermined threshold value, repeating the adjusting, the obtaining, and the determining.

10. The method of claim 6, further comprising:
    determining whether interference occurs between light emitted by a light source part and the light collected by a light collector; and
    adjusting the incident angle of light based on determining that the interference occurs.

11. A method of detecting distribution of a target material using a Raman probe configured to adjust an incident angle of light emitted by a light source part on a sample, a focal point of the light source part, a field of view of a light collector, and a focal point of the light collector, the method comprising:
    obtaining a first Raman spectrum of the sample by setting the focal point of the light collector on a surface of the sample;
    obtaining a second Raman spectrum of the sample by adjusting the field of view of the light collector;
    determining a similarity between the first Raman spectrum and the second Raman spectrum; and
    storing position information of the light source part and the light collector, and the second Raman spectrum based on the similarity being less than or equal to a predetermined threshold value.

12. The method of claim 11, wherein the obtaining of the first Raman spectrum of the sample comprises setting the focal point of the light collector on the surface of the sample by moving the light collector up and down.

13. The method of claim 11, wherein the obtaining of the second Raman spectrum of the sample comprises adjusting the field of view of the light collector by moving the light collector up and down.

14. The method of claim 11, wherein the determining of the similarity comprises determining the similarity using one of Euclidean distance, Manhattan Distance, Cosine Distance, Mahalanobis Distance, Jaccard Coefficient, Extended Jaccard Coefficient, Pearson's Correlation Coefficient, and Spearman's Correlation Coefficient.

15. The method of claim 11, further comprising:
based on the similarity being greater than the predetermined threshold value, determining whether the focal point of the light source part is the same as the focal point of the light collector; and
based on the focal point of the light source part being the same as the focal point of the light collector, repeating the obtaining of the first Raman spectrum of the sample by adjusting the focal point of the light source part, the obtaining of the second Raman spectrum of the sample, the determining of the similarity between the first Raman spectrum and the second Raman spectrum, and the determining whether the focal point of the light source part is the same as the focal point of the light collector.

16. The method of claim 15, further comprising:
based on the focal point of the light source part not being equal to the focal point of the light collector, obtaining a third Raman spectrum of the sample by adjusting the field of view of the light collector,
determining a similarity between the second Raman spectrum and the third Raman spectrum; and
storing position information of the light source part and the light collector, and the third Raman spectrum based on the determination of similarity.

* * * * *